(12) United States Patent
Edwards

(10) Patent No.: US 9,452,037 B2
(45) Date of Patent: *Sep. 27, 2016

(54) DELIVERY OF ORAL CARE PRODUCTS

(75) Inventor: Jeffrey D. Edwards, Perth (AU)

(73) Assignee: INTERNATIONAL SCIENTIFIC PTY LTD, Leederville, Western Australia (AU)

( * ) Notice: Subject to any disclaimer, the term of this patent is extended or adjusted under 35 U.S.C. 154(b) by 202 days.

This patent is subject to a terminal disclaimer.

(21) Appl. No.: 13/699,225

(22) PCT Filed: May 24, 2011

(86) PCT No.: PCT/AU2011/000619
§ 371 (c)(1),
(2), (4) Date: Feb. 18, 2013

(87) PCT Pub. No.: WO2011/146978
PCT Pub. Date: Dec. 1, 2011

(65) Prior Publication Data
US 2013/0137063 A1     May 30, 2013

(30) Foreign Application Priority Data
May 25, 2010   (AU) ................................ 2010902280

(51) Int. Cl.
*A61C 19/06*      (2006.01)
*A46B 15/00*      (2006.01)
(Continued)

(52) U.S. Cl.
CPC ......... *A61C 19/063* (2013.01); *A46B 15/0026* (2013.01); *A46D 1/0207* (2013.01); *A61C 19/066* (2013.01); *A61K 8/19* (2013.01);
(Continued)

(58) Field of Classification Search
CPC ............. A46B 15/0026; A61C 17/00; A61C 17/16–17/40; A61C 19/06; A61C 19/063; A61C 19/066; A61N 2/002; A61N 2/00; A61M 2037/0007; A61M 35/00
USPC .......................................... 433/215–216, 229
See application file for complete search history.

(56) References Cited

U.S. PATENT DOCUMENTS

| 4,079,038 A | 3/1978 | Choi et al. |
| 4,093,709 A | 6/1978 | Choi et al. |

(Continued)

FOREIGN PATENT DOCUMENTS

| AT | 7445 U2 | 4/2005 |
| JP | 06-014813 | 1/1994 |

(Continued)

OTHER PUBLICATIONS

Duckworth et al., Fluoride uptake to demineralised enamel: a comparison of sampling techniques, Caries Res., 32:417-21 (1998).
(Continued)

*Primary Examiner* — Edward Moran
(74) *Attorney, Agent, or Firm* — Marshall, Gerstein & Borun LLP

(57) ABSTRACT

A method for the delivery of an oral care active agent comprising the following step: applying an active agent(s) between a target oral biological barrier and a magnetic device comprising one or more pairs of displaced dipolar magnetic elements linked by a magnetic return wherein the magnetic return is orientated on the surfaces of the dipole pair distal to the biological barrier.

13 Claims, 15 Drawing Sheets

(51) Int. Cl.
  *A46D 1/00*   (2006.01)
  *A61K 8/19*   (2006.01)
  *A61N 2/06*   (2006.01)
  *A61Q 11/00*  (2006.01)
  *A61M 35/00*  (2006.01)

(52) U.S. Cl.
  CPC ............ *A61N2/06* (2013.01); *A61Q 11/00* (2013.01); *A46B 2200/1066* (2013.01); *A61K 2800/47* (2013.01); *A61M 35/00* (2013.01)

(56)           References Cited

U.S. PATENT DOCUMENTS

| | | | |
|---|---|---|---|
| 4,131,648 | A | 12/1978 | Choi et al. |
| 4,138,344 | A | 2/1979 | Choi et al. |
| 4,180,646 | A | 12/1979 | Choi et al. |
| 4,304,767 | A | 12/1981 | Heller et al. |
| 4,502,497 | A | 3/1985 | Siahou |
| 4,571,768 | A | 2/1986 | Kawashima |
| 4,946,931 | A | 8/1990 | Heller et al. |
| 5,785,956 | A | 7/1998 | Sullivan et al. |
| 5,800,685 | A | 9/1998 | Perrault |
| 5,968,543 | A | 10/1999 | Heller et al. |
| 6,338,751 | B1 | 1/2002 | Litkowski et al. |
| 6,383,129 | B1 * | 5/2002 | Ardizzone ............ A61N 2/06 600/15 |
| 6,413,536 | B1 | 7/2002 | Gibson et al. |
| 6,596,296 | B1 | 7/2003 | Nelson et al. |
| 6,613,355 | B2 | 9/2003 | Ng et al. |
| 6,631,294 | B2 | 10/2003 | Andino et al. |
| 6,667,371 | B2 | 12/2003 | Ng et al. |
| 6,845,272 | B1 | 1/2005 | Thomsen et al. |
| 2003/0172482 | A1 | 9/2003 | Tini |
| 2005/0255427 | A1 * | 11/2005 | Shortt et al. ............ 433/118 |
| 2007/0208209 | A1 | 9/2007 | Holcomb |
| 2009/0093669 | A1 | 4/2009 | Farone et al. |
| 2010/0212676 | A1 | 8/2010 | Shapiro et al. |

FOREIGN PATENT DOCUMENTS

| | | |
|---|---|---|
| JP | 10-192419 | 7/1998 |
| JP | H11113638 A | 4/1999 |
| JP | 2008521514 | 6/2008 |
| WO | WO-00/23144 A1 | 4/2000 |
| WO | WO2009/135246 A1 * | 11/2009 |

OTHER PUBLICATIONS

International Preliminary Report on Patentability, corresponding International Application No. PCT/AU2011/000619, dated Apr. 13, 2012.

International Search Report and Written Opinion, corresponding International Application No. PCT/AU2011/000619, mailing date Aug. 15, 2011.

Shi et al., Rapid method for the determination of trace fluoride and activation of ion-selective electrode, Anal. Sci., 19(5):671-3 (2003).

* cited by examiner

DELIVERY OF ORAL CARE PRODUCTS

CROSS-REFERENCE TO RELATED APPLICATIONS

This application is the U.S. National Stage of PCT/AU2011/000619, filed May 24, 2011, incorporated herein by reference, which claims the benefit of Australian Patent Application No. 2010902280 filed May 25, 2010.

FIELD OF THE INVENTION

The present invention relates to a method and apparatus for enhanced delivery of substances (such as pharmaceuticals, nutraceuticals, biopharmaceuticals, cosmeceutical, biologically active substances, detergents, cleaners, bleaches, dyes, fragrances, conditioners or polishes) to biological and non-biological surfaces by application of magnetic fields having distinctive, complex characteristics when such magnetic fields are stationary or in motion.

BACKGROUND ART

The delivery of active agents to surfaces must occur in sufficient amounts to allow the agent to achieve its purpose. However it can be difficult to achieve sufficient delivery of agents to a wide variety of surfaces, both biological and non-biological, due to difficulties in maintaining sufficient concentration in the operational environment and to permeability barrier effect of many target surfaces.

Furthermore, there is a general push, due to economic, health-related and environmental reasons, to use less of many active agents in a given composition. This provides further problems in relation to the delivery of active agents, as there may not be a sufficient concentration gradient to allow the active agent to diffuse effectively and to penetrate or partition into or onto the surface.

Chemical penetration enhancers can facilitate changes in barrier permeability. However, the use of chemical penetration enhancers can be problematic due to unknown interaction with the active agent and the potential for adverse side effects such as irritation of skin and mucosal surfaces or unwanted interactions with the cosmetic and or functional properties of barriers.

A diffusion enhancement technique which may be used for some biological surfaces is iontophoresis, in which an electrical energy gradient is used to accelerate the charged target active agent(s) across the skin or barrier. However, iontophoresis is only suitable to specific active agents with certain ionic structures and can be injurious to certain biological barriers due to exchange ion degradation. Additionally, iontophoresis requires the use of intimate electrical contact and adhesive electrodes, which are not suitable for all target surfaces or barriers.

Other techniques to create mobility and/or direction in the movement of active agent(s) such as magnetokinetics and magnetophoresis are possible, however they have been difficult to implement due to poor performance, high hardware and energy requirements, and cost.

There is therefore a need for methods to enhance the availability, diffusion characteristic and penetration of active agents into surfaces using physical technologies which can replace or at (east compliment the previously known chemical and physical penetration enhancers.

The present invention seeks to provide an improved delivery process for active agents that have a pharmaceutical, nutraceutical, biopharmaceutical, cosmeceutical, cosmetic, anti-biological (anti-bacterial, anti-viral, antifungal, anti-parasitic, insecticidal etc), detergent, cleaning, bleaching, dying, fragrancing, conditioning or polishing activity, in a manner which increases the directional penetration of these agents into biological and non-biological surfaces.

The previous discussion of the background art was intended to facilitate an understanding of the present invention only. The discussion is not an acknowledgement or admission that any of the material referred to is or was part of the common general knowledge as at the priority date of the application.

SUMMARY OF THE INVENTION

In accordance with a first aspect of the present invention, there is provided a method for the delivery of an oral care active agent(s) comprising the following step:
(a) applying an active agent(s) between a target oral biological barrier and a magnetic device comprising one or more pairs of displaced dipolar magnetic elements linked by a magnetic return wherein the magnetic return is orientated on the surfaces of the dipole pair distal to the biological barrier.

In accordance with a second aspect of the invention, there is provided a method for the delivery of an oral care active agent(s) comprising the following steps:
(a) applying an active agent(s) between a target oral biological barrier and a magnetic device comprising one or more pairs of displaced dipolar magnetic elements linked by a magnetic return wherein the magnetic return is orientated on the surfaces of the dipole pair distal to the biological barrier; and
(b) moving in a reciprocal, rotational or orbital manner the magnetic device so that active agents in proximity to said device will be subject to alternating polarities of magnetic flux in response to said reciprocal, rotational or orbital movement.

In accordance with a third aspect of the invention, there is provided a method for the delivery of an oral care active agent(s) comprising the following steps:
(a) applying a active agent(s) between a target oral biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements.

In accordance with a fourth aspect of the invention, there is provided a method for the delivery of an oral care active agent(s) comprising the following steps:
(a) applying a active agent(s) between a target oral biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements
(b) moving in a reciprocal, rotational or orbital manner the magnetic device so that active agents in proximity to said device will be subject to alternating polarities of magnetic field and alternating magnetic gradients in response to said reciprocal, rotational or orbital movement.

According to a form of the invention the method of the invention provides a means for driving the passage of active agent(s) across an oral biological barrier such as mucosal tissues, tooth enamel, tooth dentine and dentine tubules etc into a subject (including a patient). The method may be enhanced by the additional step of pairing the device with an alternate drug delivery system that operates either in conjunction with, or in parallel with, the device, to promote the passage of active agents through the biological barrier. Such alternate drug delivery systems may include, for example, iontophoresis, drug-adhesive matrix, chemical penetration enhancers, micro-needles and sonophoresis.

During performance of the method of the invention, the active agent(s) or a formulation including the active agent(s) is placed between the device and the subject (including a patient).

According to a particular form of the invention, the device is in the form of a brush, with the active agent located on some or all of the bristles of the brush or on the biological barrier to be brushed.

In another a form of the invention the device comprises a pad or strip within which is located a flexible or inflexible magnetic material. The pad may be reversibly applied or adhered to the biological barrier to which the active agent(s) is desired to be delivered, or may be rubbed over the biological barrier. The active agent(s) may be releasably contained within the pad or may be applied to the biological barrier prior to application or adhering of the pad to the biological barrier or rubbing of the pad over the biological barrier.

In a further form of the invention, the device comprises a mouthguard, gum shield, bite guard, guard tray etc. The active agent may be applied or be incorporated within the guard or shield prior to application over the biological barrier of the teeth and/or gums or may be applied to the biological barrier before application of the guard or shield.

In another form of the invention, the device may comprise a dental splint such as gum splint, cap splint, crib splint etc. The active agent may be located on or incorporated into the splint prior to application of the splint to the biological barrier or may be applied to the biological barrier after installation of the splint.

In another form of the invention, the device may comprise a roller applicator or pen device which can be moved or rubbed, either manually or by motorised action over the biological barrier. The active agent may be applied to or incorporated in the device prior to it being rubbed over the surface, or the active agent may be applied to the surface prior to the device being rubbed or moved over it.

Other aspects and advantages of the invention will become apparent to those skilled in the art from a review of the ensuing description, which proceeds with reference to the following illustrative drawings.

BRIEF DESCRIPTION OF THE DRAWINGS

The present invention will now be described, by way of example only, with reference to the accompanying drawings.

FIG. 2A is a diagrammatic representation of the magnetic elements. FIG. 2B is a diagrammatic representation of the polarities generated by the magnetic elements. FIG. 2C is a photograph of a magnetic film comprising two sets of displaced dipolar magnetic elements wherein the orientation of the second set is 90° to the orientation of the first set, showing the complex magnetic fields generated by the offset magnetic elements.

FIG. 3A is a diagrammatic representation of the magnetic elements. FIG. 3B is a diagrammatic representation of the polarities generated by the magnetic elements. FIG. 3C is a photograph of a magnetic film comprising two sets of displaced dipolar magnetic elements wherein the orientation of the second set is 45° to the orientation of the first set, showing the complex magnetic fields generated by the offset magnetic elements.

DESCRIPTION OF THE INVENTION

General

Figure 1A:
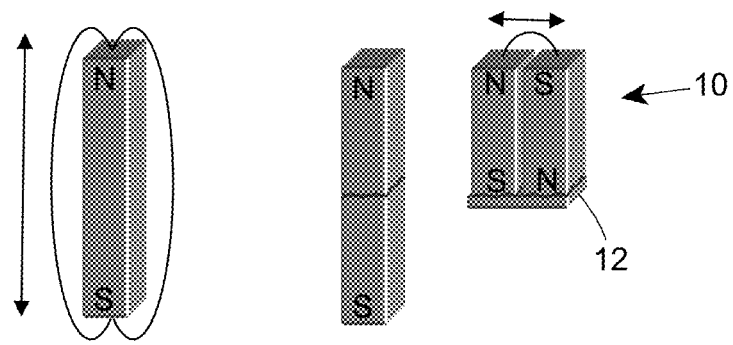
FIGS. 1A-1C depict representations of the nature of a pair of displaced dipolar magnetic elements 10 and the magnetic return 12, and various combinations and orientations (14, 16, 18, 20) of dipole pairs.
Figure 1B:
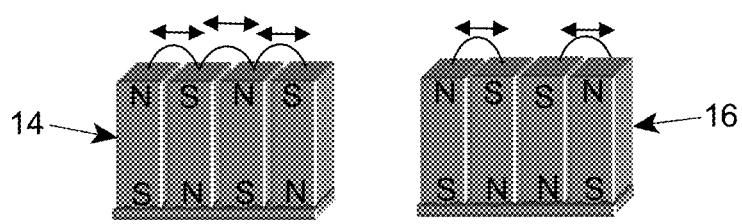
Figure 1C:
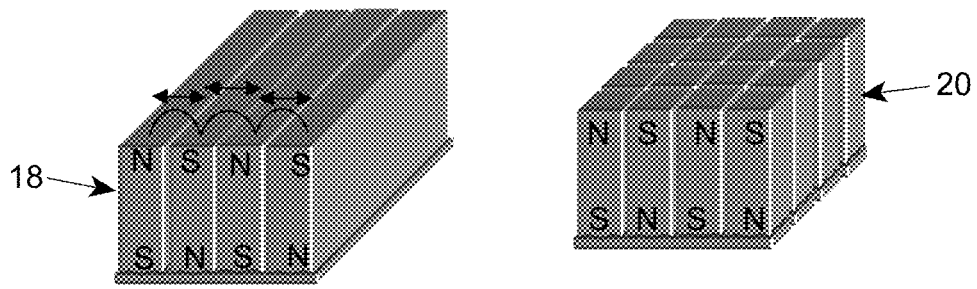

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, displacement and field strength etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Preferred Embodiments

The inventor of the present invention has revealed that the penetration of an active agent into or onto a surface such as a biological or non-biological surface can be enhanced by magnetic flux. The inventors of the present invention also reveal that certain arrangements of magnetic flux may induce thermal noise and other forms of molecular disorder, which act against such magnetic enhanced penetration. As a result only specific arrangements of magnetic elements, as disclosed by the present invention, permit the coexistence of diamagnetic repulsion enhanced diffusion of active ingredients and dielectric polarisation enhanced permeation changes.

Therefore, in accordance with a first aspect of the present invention, there is provided a method for the delivery of an oral care active agent(s) comprising the following step:
  (a) applying an active agent(s) between a target oral biological barrier and a magnetic device comprising one or more pairs of displaced dipolar magnetic elements linked by a magnetic return wherein the magnetic return is orientated on the surfaces of the dipole pair distal to the biological barrier.

In accordance with a second aspect of the invention, there is provided a method for the delivery of an oral care active agent(s) comprising the following steps:
  (a) applying an active agent(s) between a target oral biological barrier and a magnetic device comprising one or more pairs of displaced dipolar magnetic elements linked by a magnetic return wherein the magnetic return is orientated on the surfaces of the dipole pair distal to the biological barrier; and
  (b) moving in a reciprocal, rotational or orbital manner the magnetic device so that active agents in proximity to said device will be subject to alternating polarities of magnetic flux in response to said reciprocal, rotational or orbital movement.

In accordance with a third aspect of the invention, there is provided a method for the delivery of an oral care active agent(s) comprising the following step:
  (a) applying a active agent(s) between a target oral biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements.

In accordance with a fourth aspect of the invention, there is provided a method for the delivery of an oral care active agent(s) comprising the following steps:
  (a) applying a active agent(s) between a target oral biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements
  (b) moving in a reciprocal, rotational or orbital manner the magnetic device so that active agents in proximity to said device will be subject to alternating polarities of magnetic field and alternating magnetic gradients in response to said reciprocal, rotational or orbital movement.

Without being bound by any particular theory, it is believed that in general, increasing the magnetic flux beyond a certain limit does not lead to a continued increase in diamagnetic flow. Instead, above a certain level the increased magnetic flux instead leads to increased thermal noise and or other disordering processes that act contrary to diamagnetic repulsion induced diffusion enhancement. This thermal noise causes an increase in the random movement of molecules that overwhelms the diamagnetic repulsion effect created by the presence of a magnetic field.

Furthermore, the effect of a traditional uniform magnetic or electro-magnetic field on the dielectric tissues of the mouth, gum and teeth results in ionic polarization across the entire magnetic flux gradient rather than across adjacent regions. Polarization over such large distances limits the potential for enhanced micro fluidic flow. However in the case of the present invention, the use of one or more pairs of displaced dipolar magnetic elements linked by a magnetic return creates dielectric polarisation in closely adjacent regions that act to enhance micro-fluidic flow.

The present inventors have now identified that the utility of a magnetic field in enhanced delivery of active agents in oral health can be increased not just by increasing the strength of an individual magnetic field, but also by taking advantage of the differences between the flux of two magnetic fields of alternative polarity and orientation. The present invention thus allows dielectric polarization to be used to increase the permeability of target tissues in conjunction with the use of diamagnetic repulsion to enhance diffusion of active agents across barriers in such a manner that one effect does not negative the benefit of the other.

The inventors of the present invention believe that increasing the utility of the magnetic flux in this manner has a number of advantageous effects. It is known that increasing the magnetic flux increases the diamagnetic repulsion of the active agent away from the magnetic source and towards the target biological barrier. This is a feature of diamagnetic susceptibility and is related to the paired electrons of diamagnetic molecules being repelled by magnetic fields. In this way, diamagnetic repulsion provides a means of adding directionality and mobility to molecules during diffusion.

The inventors further believe that that dielectric polarization of ionic species in target barriers could act to enhance penetration of active agents through induced osmotic and ionic effects. The inventors also believe that the increased flux, particularly perpendicular magnetic flux between two opposite poles, temporarily modifies or alters the barrier function and permeability, changing the microfluidic flow without permanently changing the physical structure of the surface.

However, the inventors of the present invention also believe that the diamagnetic repulsive effects of traditional uniform magnetic and electromagnetic fields tend to act contrary to the dielectric polarisation and therefore tend to cancel any benefit. The inventors of the present invention thus believe that the present invention, comprising various arrangements of displaced dipolar magnetic pairs, allows diamagnetic repulsion to be maintained in the presence of dielectric polarization, thus providing an effective means of influencing molecular movement and permeation enhancements of barriers during the delivery of active agents.

This can be achieved by:
(a) juxtaposing two or more magnetic fields generated by one or more pairs of displaced dipolar magnetic elements linked by a magnetic return to achieve a spatially varying gradient of magnetic flux;

(b) moving two or more magnetic fields generated by one or more pairs of displaced dipolar magnetic elements linked by a magnetic return over a fixed point to achieve a temporally varying gradient of magnetic flux, or (c) a combination of (a) and (b).

Each pair of displaced dipolar magnetic elements of the present invention may, for the purposes of visualisation, be thought of in terms of a single traditional rod dipolar magnetic that is cleaved or broken around its central point and the two resulting sections rotated through 180° and brought together such that the opposite poles are adjacent (see, for example, FIG. 1A). The magnetic return is used to integrate the magnetic fields at the point of cleavage. The result is a dipolar pair, displaced horizontally so as to provide both a perpendicular and a horizontal magnetic flux gradient.

In each pair of displaced dipolar magnetic elements, each individual dipole provides diamagnetic repulsion to the active agents which are to be transported across the biological barrier, whilst the horizontal flux between each dipole pair acts to polarize the dielectric properties of the target tissue, inducing permeation changes.

The device of the present invention may comprise one pair of displaced dipolar magnetic elements, or may preferably comprise a number of pairs of displaced dipolar magnetic elements. For example, FIGS. 1A-1B show a variety of arrangements (14, 16, 18, of dipole pairs, arranged in rows or grids. The terms "pair" and "pairs" are used variously in the present specification, and reference to a single pair of displaced dipolar magnetic elements may be taken to also refer to multiple pairs of displaced dipolar magnetic elements.

The polarity of one pair of displaced dipolar magnetic elements may be in the same orientation as that of the neighbouring pair of displaced dipolar magnetic elements (i.e. the series may comprise [NS][NS][NS] (14)) or may be in the opposite orientation (i.e. the series may comprise [NS][SN][NS] (16)) (see FIG. 1B).

There is also provided by the present invention use of a magnetic device for the delivery of an oral care active agent(s) comprising:

(a) applying an active agent(s) between a target biological barrier and a magnetic device comprising one or more pairs of displaced dipolar magnetic elements linked by a magnetic return wherein the magnetic return is orientated on the surfaces of the dipole pair distal to the biological barrier.

There is further provided use of a magnetic device for the delivery of an oral care active agent(s) comprising:

(a) applying an active agent(s) between a target biological barrier and a magnetic device comprising one or more pairs of displaced dipolar magnetic elements (inked by a magnetic return wherein the magnetic return is orientated on the surfaces of the dipole pair distal to the biological barrier; and (b) moving in a reciprocal, rotational or orbital manner the magnetic device so that active agents in proximity to said device will be subject to alternating polarities of magnetic flux in response to said reciprocal, rotational or orbital movement.

In addition, there is provided use of a magnetic device for the delivery of an oral care active agent(s) comprising:

(a) applying a active agent(s) between a target biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements.

Finally, there is provided use of a magnetic device for the delivery of an oral care active agent(s) comprising:
  (a) applying a active agent(s) between a target biological barrier and a magnetic device comprising at least two sets of pairs of displaced dipolar magnetic elements linked by a magnetic return wherein the magnetic return is orientated on the surfaces of the dipole pair distal to the biological barrier and wherein the alignment of the first set of displaced dipolar magnetic elements is angularly offset relative to the alignment of the second set of displaced dipolar magnetic elements
  (b) moving in a reciprocal, rotational or orbital manner the magnetic device so that active agents in proximity to said device will be subject to alternating polarities of magnetic field and alternating magnetic gradients in response to said reciprocal, rotational or orbital movement.

Preferably the uses provided above allow the improved and increased penetration of the active agents into the biological barrier. Most preferably, such improved and increased penetration of the active agents leads to improved action of the active agent(s), which in turn leads to improved oral health or cosmetic outcomes. For example, use of the present invention to increase the penetration of fluoride into a tooth surface may lead to an improvement in oral health by decreasing the incidence of dental caries, or use of the invention to increase the penetration of carbamide peroxide may lead to an improvement in the cosmetic appearance of teeth by increasing the whitening effect.

A magnetic return according to the present invention is a member that is adjacent to one surface of each of the members of the dipolar pair, passing from the positive polar surface of one of the pair of displaced dipolar magnetic elements to the negative polar surface of the other member of the pair of displaced dipolar magnetic elements wherein the magnetic return integrates the magnetic fields on those surfaces and reduces or eliminates the magnetic flux on those surfaces. The magnetic return may extend further to unite one set of dipole pairs with another set of dipole pairs, or a larger group of dipole pairs. The magnetic return is preferably located on the surfaces of the dipole pair distal to the biological surface to which the magnetic fields are desired to be applied.

The magnetic return can be composed of any material that is magnetically conductive. Preferably, the material is a ferromagnetic material such as an iron compound (e.g. a ferrite such as barium ferrite, magnetite, or mild steel), a cobalt material, a strontium material, a barium material or a nickel material. The material may have a metalloid component such as boron, carbon, silicon, phosphorus or aluminium. Rare earth material such as neodymium or samarium may also be used.

The magnetic return preferably links the pair of displaced dipolar magnetic elements by covering all or at least some of one polar surface of the first magnet of the pair, and all or at least some of the opposite polar surface of the second magnet of the pair.

The device may also comprise a housing for the pairs of displaced dipolar magnetic elements. Preferably; the housing does not interfere with the generated magnetic fields.

The movement described herein may be either through manual operation or through mechanical means. Where the movement is delivered through manual operation (i.e., through normal consumer actions such as brushing or scrubbing) is used to mobilize the magnetic device the frequency will be in the order of 1 Hz to 5 Hz. In such cases, the strength of the magnet field produced by each element of the magnet array should be between about 100 and 500 Gauss. In the alternate, where movement is delivered through mechanical or electrical means, depicted representationally as box 40 in FIGS. 4, 5A, 5B, and 6 (such as in the form of an electrical brush like an electrical tooth brush) the oscillation should be in the order of approximately 100 and 8,000 Hz with a magnet flux of between about 100 and 1000 Gauss.

As used herein, rotational includes movement in an arc-like, semi-circular, circular or orbital manner.

In a particular form of the invention the magnetic device includes a means for moving the magnetic device over the biological barrier. Such a means will include any mechanism, electronic or mechanical, adapted for reciprocal or rotational movement of the magnetic material. For example, the magnetic material may be associated with a drive mechanism that is capable of reciprocal movement.

According to the invention, magnetic materials include, without limitation:
  a. arrangements where individual segments or sections of magnetized ferromagnetic materials are assembled in the configuration described herein; and
  b. arrangements where magnetic particles or elements are disposed in a solid or semi-solid matrix or base and the required magnetic pattern is impressed upon the ferromagnetic particles.

The present invention may be constructed using a range of magnetic materials exhibiting ferromagnetic properties. Such materials may include Iron, Strontium, Barium, Cobalt or Nickel with a metalloid component such as Boron, Carbon, Silicon, Phosphorus or Aluminium. Alternately, rare-earth materials such as Neodymium or Samarium-cobalt may also be used. Such ferromagnetic materials may be deployed as rigid elements within a device or encapsulated in a flexible matrix such as rubber or silicone.

Generally, each pair of displaced dipolar magnetic elements of the present invention has a horizontal offset between centres of between 1 and 10 millimeters, preferably 3 and 7 millimeters. As a result, pairs of displaced dipolar magnetic elements may be disposed at a repetition rate of between 2 and 10 dipolar pairs per centimeter, more preferably 1.5 and 4 dipolar pairs per centimeter.

Preferably, the poles in a particular spatial region are between 1.0 mm to 10 mm apart, more preferably, the poles are between 1.0 mm to 5.0 mm apart.

In another aspect of the invention, the magnetic flux of each magnetic pole is between about 10 Gauss and about 1000 Gauss. Preferably, the flux of each pole is between about 100 Gauss to about 600 Gauss, most preferably about 125 to 450 Gauss.

In another aspect, the difference or delta flux between the magnetic flux of two adjacent poles of opposite polarity is between about 100 Gauss and about 2000 Gauss. More preferably, the difference between the magnetic flux of two adjacent poles of opposite polarity is between about 200 Gauss to about 1400 Gauss, most preferably about 200 to 900 Gauss.

Figure 2A:
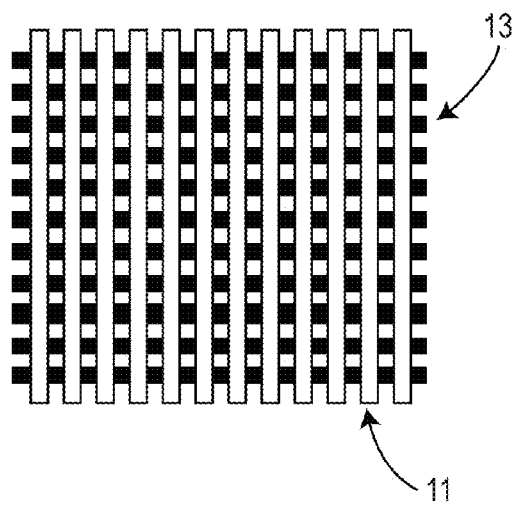
FIGS. 2A, 2B, and 2C provide an example of a device according to the present invention which consists of two sets 11, 13 of pairs of displaced dipolar magnetic elements wherein the orientation of the second 13 set is 90° to the orientation of the first set 11.
Figure 2B:
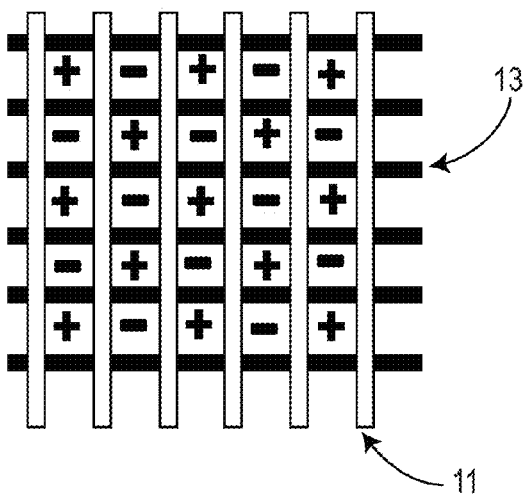
Figure 2C:
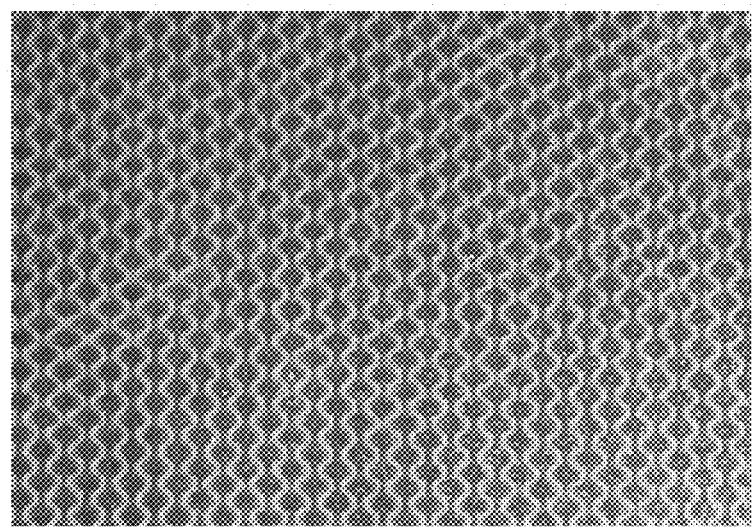
Figure 3A:
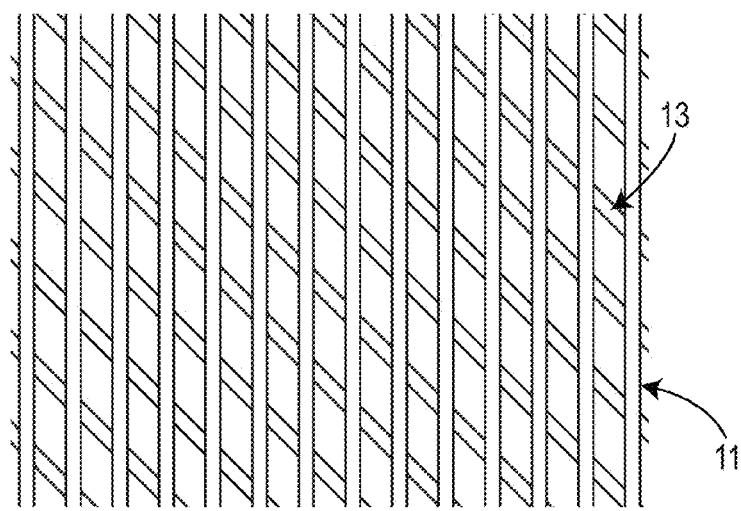
FIGS. 3A, 3B, and 3C provide an example of a device according to the present invention which consists of two sets 11, 13 of pairs of displaced dipolar magnetic elements wherein the orientation of the second set 13 is 45° to the orientation of the first set 11.
Figure 3B:
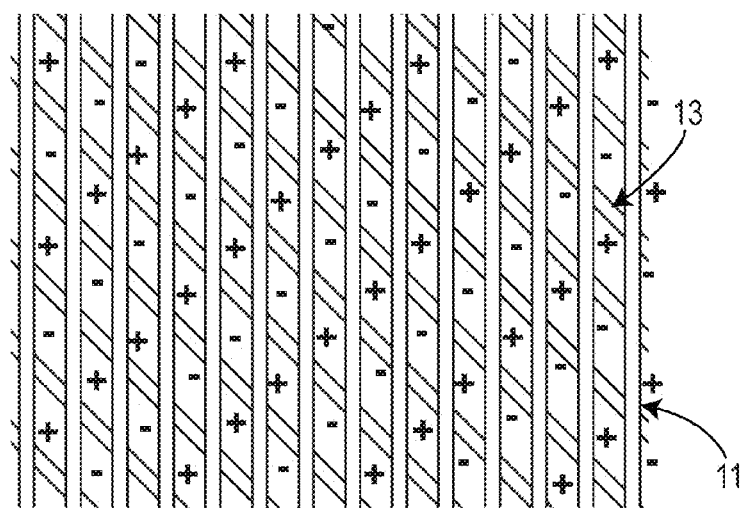
Figure 3C:
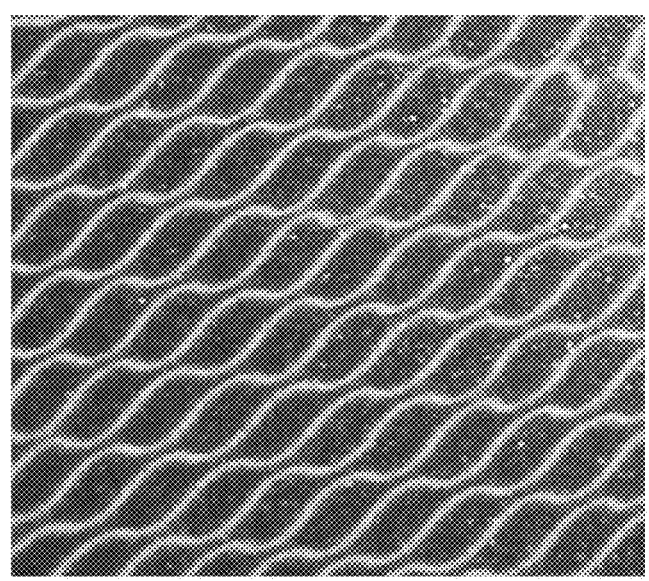
Figure 4:
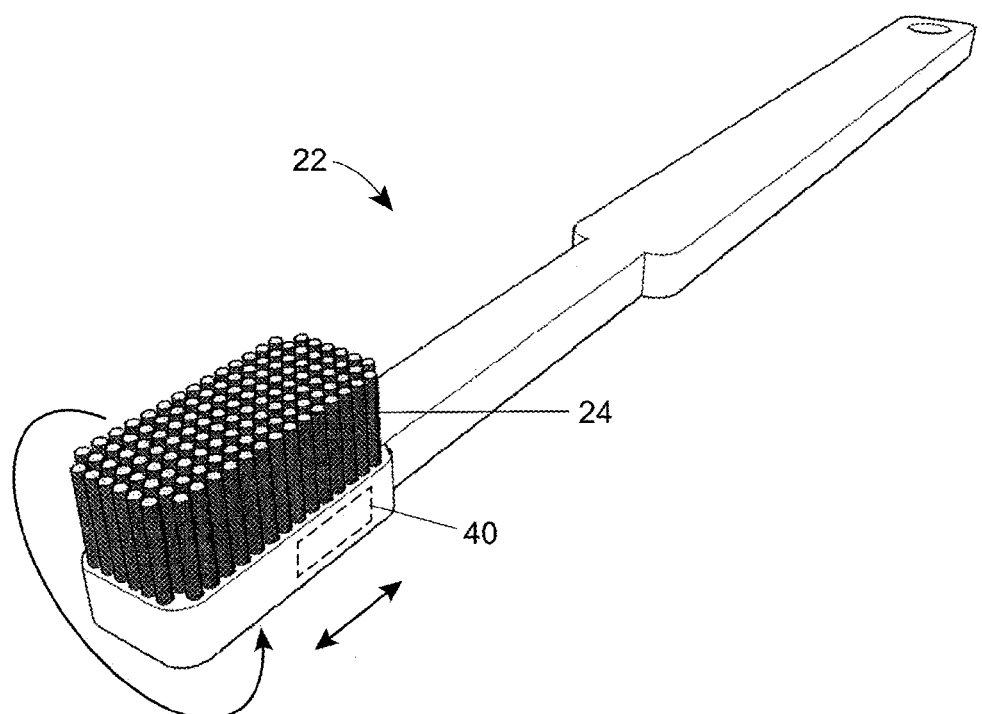
FIG. 4 depicts an example of a toothbrush 22 comprising the device of the invention, wherein the pairs of displaced dipolar magnetic elements 24 are laminated to a handle body such that they replace the role of bristles.
Figure 5A:
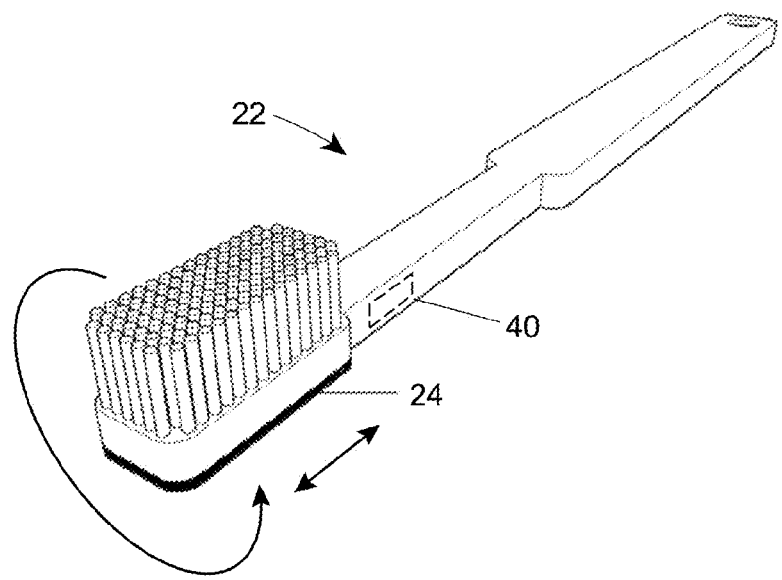
FIGS. 5A and 5B depict examples of a toothbrush 22 comprising the device of the invention, wherein the pairs of displaced dipolar magnetic elements 24 are provided is a sheet-like arrangement within the head of the brush. The pairs of displaced dipolar magnetic elements may be located immediately between the bristles of the brush and the head of the brush (FIG. 5B) or may be located distal to the head of the brush from the bristles (FIG. 5A).
Figure 5B:
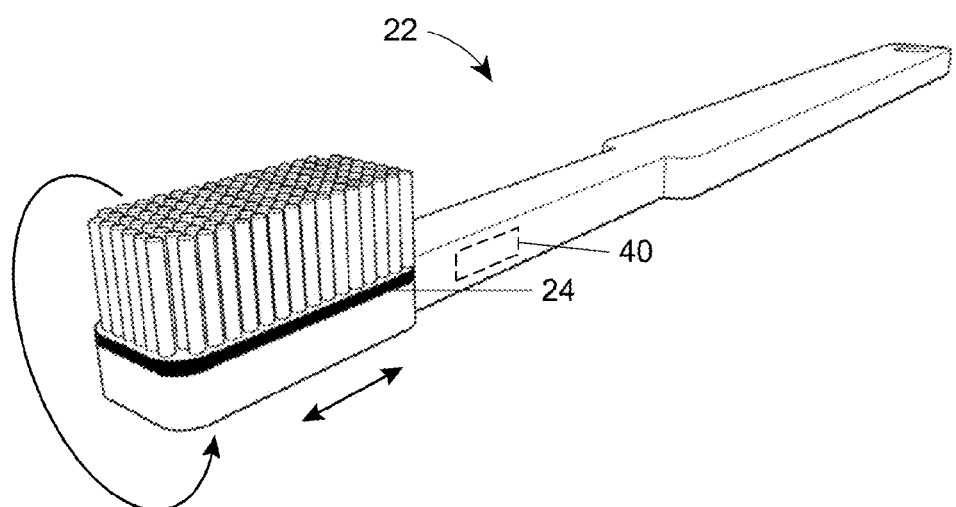
Figure 6:
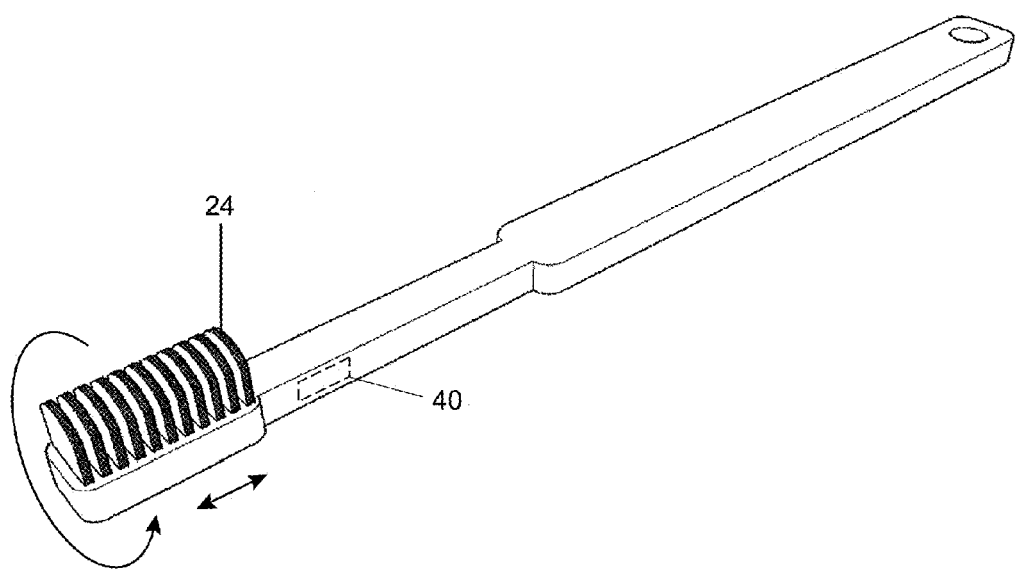
FIG. 6 depicts an example of a toothbrush 22 comprising the device of the invention, wherein the traditional monofilament bristles of the brush have been replaced with panels or sheets of pairs of displaced dipolar magnetic elements 24 in accordance with the present invention.
Figure 7:
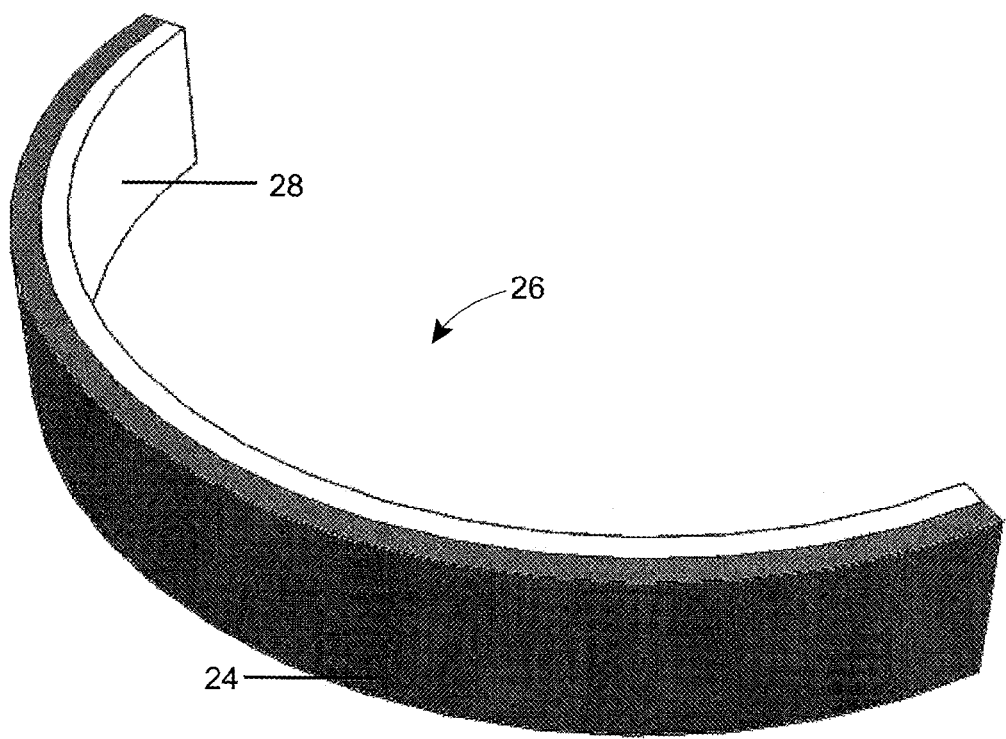
FIG. 7 depicts an example of a gum splint 26 comprising the device of the invention, wherein the pairs of displaced dipolar magnetic elements 24 are located within the semi-flexible splint and the active agents 28 are located in a matrix layer which would, in use, be located between the magnetic elements and the tooth surface.

When the magnetic device comprises at least two sets of pairs of displaced dipolar magnetic elements wherein the alignment of the first set of displaced dipolar magnetic elements is angularly offset relative to the alignment of the second set of displaced dipolar magnetic elements, the orientation of the first set of dipolar pairs is preferably between about 1° and 90° relative to the second set of dipole pairs. Preferably, the degree of angular offset is at least 10°, more preferably at least 45°, most preferably between about 45° and 90°. FIGS. 2 and 3 provide examples of arrangements of sets of pairs of displaced dipolar magnetic elements.

Such magnetic devices with at least two sets of pairs of displaced magnetic elements may have a different number of dipolar pairs disposed in the first set from that in the second set. For example, the first set of dipolar pairs may have two dipolar pairs per centimeter whilst the second set may have five dipolar pairs per centimeter.

Where a different number of dipolar pairs is used in each set of dipolar pairs in differing orientations, the magnetic fields will be complex and exhibit different flux densities in each orientation, as the fields produced by the first set of dipolar pairs will sum with that of the second set of dipolar pairs at the points of constructive and destructive interference and by doing so provide a net field of higher magnetic strength, higher magnet flux and higher magnetic gradient, all of which will add to the utility of the present invention.

The purpose of multiple intersection orientations is two-fold:
  (i) To accommodate non-linear movements either by users or by devices. Then induction effect is reliant on the target barrier being influenced by an alternating field, which only happens when the device is tracked across the barrier at 90° to the alignment of the elements. To accommodate a circular motion, the arrays are aligned so to produce an AC like induction, irrespective of the direction of motion; and
  (ii) To induce opposing charges in adjacent areas of the barrier so to produce streaming potentials to accommodate pathways that are not perpendicular to the field flux, such as vertical shunts or pathways.

The device may further comprise more than two sets of dipolar pairs. The orientation of these further sets of pairs of displaced dipolar magnetic elements may align with the first set of pairs of displaced dipolar magnetic elements and thus be angularly offset to the second set of pairs of displaced dipolar magnetic elements, or may align with, the second set and thus be angularly offset to the first set of pairs of displaced dipolar magnetic elements. Further orientations and arrangements of sets of pairs of displaced dipolar magnetic elements may be provided which align with either the first or second sets of displaced dipolar magnetic elements. For example, a many layered device may be provided which comprises a number of orientation of pairs of displaced dipolar magnetic elements stacked on top of each other, each one aligned in a different orientation to the array below (e.g. each set aligned perpendicular to the set below).

In one embodiment of this invention the target surface is an oral biological barrier, such as, for example teeth, gums and the like. In this form of the invention the device is preferentially adapted to deliver active agent(s) across the oral biological barrier. Such oral biological barriers may have micro channels, apertures, pores etc through which active agents can be delivered.

The active agents to be delivered using the method of the present invention may be delivered to the enamel, dentine, pulp, cementum, gum, or bone, via penetration of the tooth dentine, enamel surface or the gum surface.

According to a form of the invention the method of invention provides a means for driving the passage of active agent(s) across the barrier formed by a target oral biological barrier such as a mucosal surface or tooth enamel etc into a subject (including a patient). The method may be enhanced by the additional step of pairing the device with an alternate drug delivery system that operates either in conjunction with, or in parallel with, the device, to promote the passage of active agents through the biological barrier. Such alternate drug delivery systems may include, for example, iontophoresis, drug-adhesive matrix, chemical penetration enhancers, micro-needles and sonophoresis.

The process of enhanced delivery by the present invention involves the utilization of magnetic principles to apply force upon active agent(s) in such a manner as to ensure that the force acting upon the agents is different from that acting upon the molecules of the vehicle, gel or solvent. As a result, another method of improving the utility of the invention is to select or chemically alter the diamagnetic sensitivity of the active agent or that of the vehicle, gel or solvent in which it is located with the view to enhancing the differences in diamagnetic sensitivity between the two entities. By way of example, the additional of a light ester such as phenxyethyl acrylate to a diethylaminoethyl acrylate polymer may act to increase the diamagnetic susceptibility of the polymer and by doing so increase the delivery of a diamagnetic target molecule from that vehicle, gel or solvent.

According to a particular form of the invention, the device is in the form of an adhesive tooth strip, comprising a plurality of displaced dipolar magnetic pairs in planar sheet format with an active ingredient entrapped or dissolved in a drug-in-adhesive matrix. The device as disclosed may adhere to the teeth. In such form, the plurality of displaced dipolar magnetic pairs will act upon the active ingredient enhancing diffusion form the drug in adhesive matrix and enhanced delivery and bioavailability at an oral barrier whose permeability has been alter by the magnetic effects of displaced dipolar magnetic pairs.

In another a form of the invention the device is formed as a brush, with the active agent located on some or all of the bristles of the brush or applied separately to the biological barrier to be brushed.

If the device of the invention is in the form of a brush, then the displaced dipolar magnetic pairs may be used as a form of the body, as a component of the bristles or as a form of the body in which the magnetic effect is transmitted through the bristles by nature of their magnetic conductivity. In such cases the active agent can enter the biological barrier when the bristles are contacted with the biological barrier or in response to the effects of displaced dipolar magnetic pairs remotely located but whose effect is transmitted by said bristles. In a desirable form, the device of the invention is provided in the form of a manual or electrically operate toothbrush device, with the magnetic materials located in the head of the brush near the base of the bristles and the active agent being located on the bristles of the brush device. As the toothbrush is moved over the surface of the tooth, the moving magnetic field enhances the ability of the active agent to penetrate the biological barrier of the tooth.

In another a form of the invention, the device comprises a pad within which is located a flexible or inflexible magnetic material. The pad may be reversibly applied or adhered to the biological barrier to which the active agents is desired to be delivered. Alternatively, the patch- or pad-like device may be rubbed over the biological barrier. If movement is used, the movement of the pad comprising the magnetic component enhances the penetration of the active agents in accordance with the method of the present invention.

The active agent may be releasably contained within the pad, with the active agent(s) present within the pad, permeating the pad and being capable of diffusing out of the pad and penetrating the biological barrier. Alternatively, the active agents may be applied to the biological barrier prior to application or adhering of the pad to the biological barrier or prior to rubbing of the pad over the biological barrier.

In a further form of the invention, the device comprises a mouthguard, gum shield, bite guard, guard tray etc. The active agent may be applied within the guard or shield prior to application over the biological barrier of the teeth and/or gums or may be applied to the biological barrier before application of the guard or shield.

In another form of the invention, the device may comprise a dental splint such as gum splint, cap splint, crib splint etc. The active agent may be located on the splint prior to application of the splint to the biological barrier or may be applied to the biological barrier after installation of the splint. For example, the active agent may be provided in the form of an adhesive to keep the splint in a desirable location, or the drug may be delivered in a toothpaste formulation applied to the teeth either prior to application of the splint or routinely after application of the splint.

In another form of the invention, the device may comprise a roller applicator or pen device which can be moved or rubbed over the biological barrier. The active agent may be applied to the device prior to it being rubbed over the surface, or the active agent may be applied to the surface prior to the device being rubbed or moved over it.

In a further form of the invention, the device may include a polymer coating comprising a backing layer that is substantially impermeable to active substances located adjacent the magnetic material.

The active agent(s) delivered by the device of the invention may cover the entire region of the contact zone between the device and the oral biological barrier or alternatively may be formed in islands therein. In a preferred form, the active agent(s) are located between the inventive device and a subject's biological barrier.

Non-limiting examples of active agents which could be delivered using the method of the present invention to, for example, the tooth surface such as the tooth enamel include:
  a) Tooth whitening and bleaching agents: peroxides such as carbamide peroxide or hydrogen peroxide, urea peroxide, sodium percarbonate, and PVP-$H_2O_2$, enzymes etc;
  b) Anti-tartar/anti-calculus agents and anti-staining agents: anti-attachment agents such as ethyl lauroyl arginine NCl, pyrophosphates such as tetrasodium pyrophosphate, polyphosphates, polyvinylphosphonic acid, PVM/MA copolymer; enzymes, such as those used for plaque disruption, anionic polymers especially carboxylate group functionalized polymers, metal ions such as zinc salts including zinc citrate;
  c) Agents to reduce or prevent caries and/or remineralisation agents: fluoride in the form of sodium fluoride, sodium monofluorophosphate, stannous fluoride, supercharged fluoride delivery ingredients (such as dicalcium phosphate dihydrate and others disclosed in U.S. Pat. No. 5,785,956), peptides, calcium, phosphate, xylitol;
  d) Agents to reduce or prevent sensitive teeth: potassium salts such as potassium nitrate, strontium salts such as strontium chloride, stannous fluoride, sodium silicate, and bioactive glass (such as those disclosed in U.S. Pat. No. 6,338,751), polymers etc.

Non-limiting examples of active agents which could be delivered using the method of the present invention to, for example, the mucosal surface such as the gum include:
  a) Agents to treat sensitive gums: anti-inflammatories, metal ions etc and gum health actives, including those which reduce inflammation pathways and/or interfere in bacterial processes which produce inflammatory stimuli, such as Univestin (Unigen Pharma), bachalin, polyphenols, ethyl pyruvate, green tea extracts, rosemary extracts and other herbal extracts, and guanidinoethyl disulfide;
  b) Agents to treat gum diseases such as periodontitis, gingivitis: antibacterial agents such as chlorhexidine, cetyl pyridininum chloride, triclosan and magnolia extract, anti-inflammatories, metal ions such as zinc salts etc;
  c) Agents to treat aphthous ulcers: antibacterials, anti-fungals such as nystatin (Mycostatin®) or fluconazole (Difiucan®), anti-virals such as acyclovir, anti-inflammatories, vitamen B12, metal ions such as sodium bicarbonate, corticosteroid preparations such as hydrocortisone hemisuccinate, triamcinolone acetonide or prednisone;
  d) Agents to treat lichen planus: antibacterials, anti-fungals, anti-inflammatories, metal ions etc
  e) Agents to treat Burning Mouth Syndrome: anti-inflammatories, anti-fungals such as nystatin (Mycostatin) or fluconazole (Diflucan), metal ions, alpha-lipoic acid etc.

Additional agents that could be delivered to the oral surfaces include nutritional type ingredients, such as vitamins, minerals, amino acids, vitamin E, and folic acid; sensate ingredients, such as those providing cooling (such as menthol), tingle, or heat sensations (such as capsaicin or capsicum oil); flavours and flavour ingredients; colorants or other aesthetic agents; and combinations thereof. Examples of flavours and flavour ingredients include essential oils, menthol, carvone, and anethole, and various flavouring aldehydes, esters, and alcohols. Examples of essential oils include oils of spearmint, peppermint, wintergreen, sassafras, clove, sage, eucalyptus, marjoram, cinnamon, lemon, lime, grapefruit, and orange.

The above list of active agent(s) may be applied in a controlled manner, using the method of the present invention. This list is not exhaustive. Preferably, any active agent(s) that can be delivered systemically or topically can potentially be delivered using the present invention.

It is to be understood that each of the agents described above (and other agents known to the skilled addressee) can be delivered to both the tooth surface and the oral mucosal surface. Thus, for example, the anti-inflammatory agents may be delivered to either the mucosal surface, the tooth surface or both.

The active agent may be in the form of a gel, paste, liquid, thermo-reversible gel or paste, etc. For example, the active agent(s) may be in the form of toothpaste or tooth gel.

While the active agent(s) may be provided and used alone with the device, in many situations the active agent will be included in a formulation either alone or in combination with one or more other active agents. Where the formulation is to provide a pharmaceutical and/or biopharmaceutical benefit, the number of active agent(s) included in the formulation may preferentially be quite selective. Where the formulation provides a nutraceuticals, cosmetic and/or cosmeceutical effect, the number of active agents may be much greater in number.

The formulation employed in the delivery process may include additives such as other buffers, diluents, carriers, adjuvants or excipients. Any pharmacologically acceptable buffer that is magnetically inert or neutral or which has a magnetic susceptibility that is either paramagnetic in nature or greater than that of the active agent(s) being delivered, may be used, e.g., tris or phosphate buffers. Other agents may be employed in the formulation for a variety of purposes. For example, buffering agents, preservatives, co-solvents, surfactants, oils, humectants, emollients, chelating agents, stabilizers or antioxidants may be employed. Water soluble preservatives which may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. A surfactant may be Tween 80. Other vehicles that may be used include, but are not limited to, polyvinyl alcohol, povidone, hydroxypropyl methyl cellulose, poloxamers, carboxymethyl cellulose, hydroxyethyl cellulose, purified water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylated hydroxyanisole, butylated hydroxytoluene, etc.

The indications, effective doses, contra-indications, vendors etc, of the active agents in the formulations are available or are known to one skilled in the art.

The active agents may be present in individual amounts of from about 0.001 to about 5% by weight and preferably about 0.01% to about 2% by weight. However, it is contemplated that the active agents may be present in individual amounts greater than this, for example up to 100%.

Suitable water soluble buffering agents that may be employed include sodium carbonate, sodium borate, sodium phosphate, sodium acetate, sodium bicarbonate, etc., as approved by the US FDA for the desired route of administration. These agents may be present in amounts sufficient to maintain a pH of the system of between about 2 to about 9, preferably about 4 to about 8, more preferably 4.5, 5, 5.5, 6, 6.5, 7 or 7.5 (or any pH in between). As such the buffering agent may be as much as about 5% on a weight to weight basis of the total formulation. Electrolytes such as, but not limited to, sodium chloride and potassium chloride may also be included in the formulation where appropriate.

The active agents to be delivered using the device of the present invention may be provided in a matrix layer. If the active agent delivered by the device of the present invention is contained within a matrix, the matrix preferably allows the active agent to diffuse or exit the matrix in some manner and contact the biological barrier, perhaps by moving down the bristles of the brush to the biological barrier.

The matrix is preferentially prepared from a polymer or copolymer prepared from e.g., polyisobutylene, ester of polyvinyl alcohol, polyacrylic and polymethacrylic acid esters, natural rubber, polymers of styrene, isoprene, and styrene-butadiene or silicone polymers, resin components, such as, saturated and unsaturated hydrocarbon resins, derivatives of abietyl alcohol and of beta-pinene, plasticizers, such as phthalic acid esters, triglycerides and fatty acids, as well as a series of other substances known to those skilled in the art.

Matrix biocompatible polymers that might be used in the invention include compounds such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety.

The matrix containing the active agents may also be prepared from thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

The matrix may also be a hydrogel, being a gel prepared with hydrophilic polymers, and these materials are well known in the art, frequently being used as part of biomedical electrodes, such as are described in U.S. Pat. Nos. 6,631,294 and 6,845,272, the contents of which are incorporated herein by reference. Examples of hydrophilic polymers useful for the preparation of hydrogels are polyacrylate, polymethacrylate, polyacrylamide, polyvinyl alcohol), poly(ethylene oxide), poly(ethylene imine), carboxy-methylcellulose, methylcellulose, polyacrylamide sulphonic acid), polyacrylonitrile, poly(vinyl-pyrrolidone), agar, dextran, dextrin, carrageenan, xanthan, and guar. The preferred hydrogels are acrylates and may be, for example, preferably made from acrylic esters of quaternary chlorides and/or sulfates or acrylic amides of quaternary chlorides; polymers of this type are disclosed in U.S. Pat. No. 5,800,685, incorporated herein by reference. The hydrophilic polymers will generally constitute from about 1 to about 70%, preferably about 5 to about 60%, more preferably about 10 to about 50%, by weight of the hydrogel.

In a highly preferred form of the invention, a topical formulation for delivery to a subject is prepared by selecting a desired amount of active agent. The agent is then preferably placed in a suitable delivery matrix. The amount of the active agent to be administered and the concentration of the compound in the topical formulation depends upon the diluent, delivery system or device selected, the clinical or cosmetic condition of the subject, the side effects and the stability of the active agent in the matrix.

Non-Limiting Illustration of the Invention

Further features of the present invention are more fully described in the following non-limiting Examples. This description is included solely for the purposes of exemplifying the present invention. It should not be understood as a restriction on the broad description of the invention as set out above.

Example 1

The ability of the devices of the present invention to deliver active agents (carbamide peroxide) through the dentine of teeth was tested.

20 human teeth were donated by a registered oral surgeon and stored in alcohol for 48 hours prior to ultrasonic cleaning and drying using warm air and absorbent paper. Teeth were divided into two groups. 10 teeth were allocated to the active group (exposed to pairs of displaced dipolar magnetic elements in motion) and 10 allocated to the passive delivery group (exposed to materials with no magnetic field but also in motion). Size, colour and degree of degeneration were matched between the groups.

Individual teeth were photographed using controlled light conditions before and after application of Carbamide Peroxide Gel using a 10 megapixel camera (Pentax Optio) digital camera. Commercial digital imaging software (Photoshop CS2 version 9), was used in CMYK mode to degenerate histograms and images of matched regions of enamel in tooth before and after application.

Each tooth was treated using 700 mg of 36% Carbaminde Peroxide based Tooth Whitening gel. This measure of gel was place on the surface of 10 sized matched pairs of displaced dipolar magnetic elements comprising flexible ETP008 magnetic material formed of a parallel linear array of displaced dipolar magnetic elements with common pole pairs of 450 gauss peak flux with a centre to centre spatial separation of 4 mm oscillated by electrical motor at a frequency of 3 Hz [this is also known as the field-in-motion or FIM group, or eM patch group]. The control group was placed on the surface of polystyrene cards and also oscillated at 3 Hz using the same motorized oscillation means. Teeth were placed horizontally into the carbamide peroxide gel mounds ensuring complete contact and coverage. After 3 minutes of exposure, teeth were removed, cleaned and preserved for the following day. This was repeated for 5 consecutive days.

Analysis was conducted using three measures of colour change. Relative change in percentage of yellow in the image, changes in the spectrum shift from yellow to white and in the luminosity level.

Relative change in the percentage of Yellow in the matched regions of enamel was taken as reflecting the change in the colour of the underlying dentin materials. Differences in the relative change in the Yellow spectrum were interpreted as reflecting the different penetrations rates of peroxide delivery through the enamel under active and passive conditions.

Changes in the spectrum medium point reflects change in colour from the yellow towards the white end of the spectrum. Again, differences in spectrum medium point location were interpreted as reflecting the different penetrations rates of peroxide delivery through the enamel under active and passive conditions.

Luminosity was recorded as a measure of brightness with changes reflecting different penetrations rates of peroxide delivery through the enamel under active and passive conditions.

Figure 10:
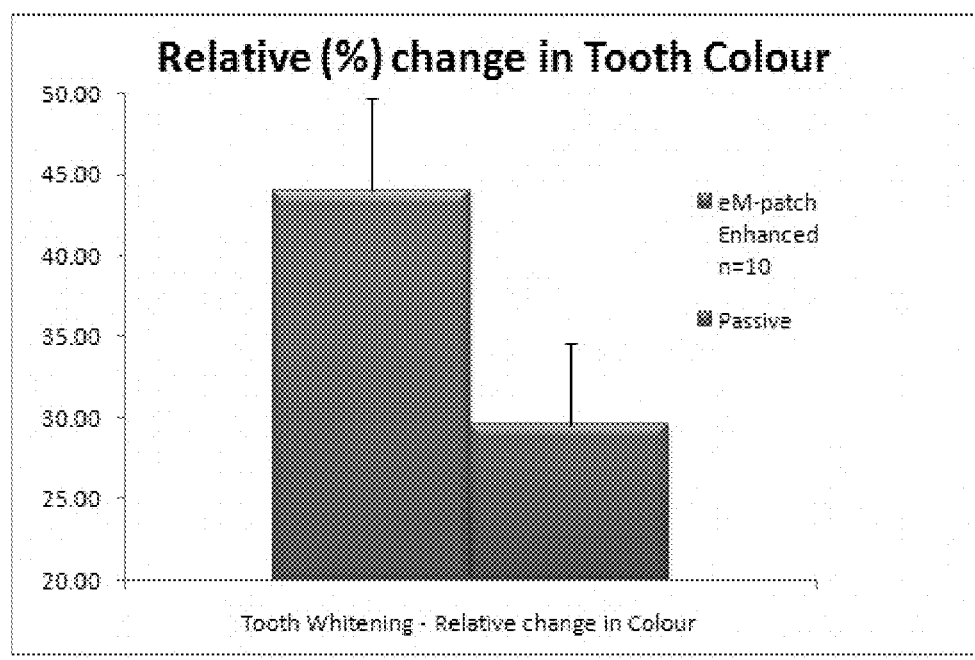
FIG. 10 is a graph of the relative (%) change in tooth colour of teeth treated with carbamide peroxide delivered passively or by a device of the present invention.

Changes in tooth colour were determined by examining the percentage of the mean yellow in the digital image histogram. The analysis revealed that the group exposed to the pairs of displaced dipolar magnetic elements in motion achieved a 49% (p=0.025) greater reduction in yellow content compared to the passive Carbamide peroxide group (Table 1 and FIG. 10).

TABLE 1

|  | Magnetic FIM (eM-patch) | Passive |
|---|---|---|
| Mean | 43.98 | 29.58 |
| Stdev | 16.21 | 14.35 |
| Sem | 5.73 | 5.07 |

$p = 0.025$

Figure 8:
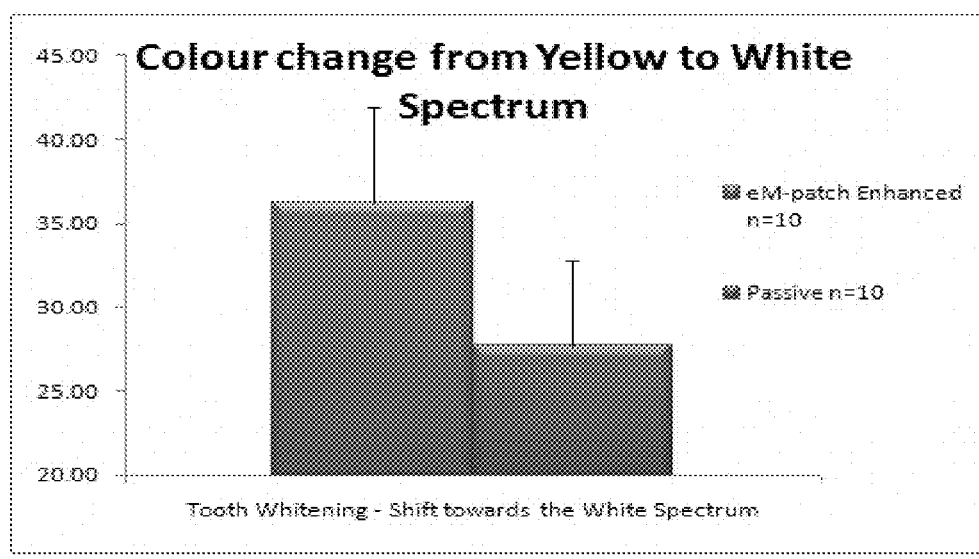
FIG. 8 is a graph of the average shift from the yellow spectrum to the white spectrum of teeth treated with carbamide peroxide delivered passively or by a device of the present invention.

Analysis of the colour spectrum shift for each tooth revealed that the average shift from the yellow spectrum to the white spectrum was 31% greater in the group exposed to the pairs of displaced dipolar magnetic elements in motion than the passive diffusion group (Table 2 and FIG. 8).

TABLE 2

|  | Magnetic FIM (eM-patch) | Passive |
|---|---|---|
| Mean | 36.20 | 27.70 |
| Stdev | 8.20 | 12.40 |
| Sem | 2.90 | 4.38 |

$p = 0.044$

Figure 9:
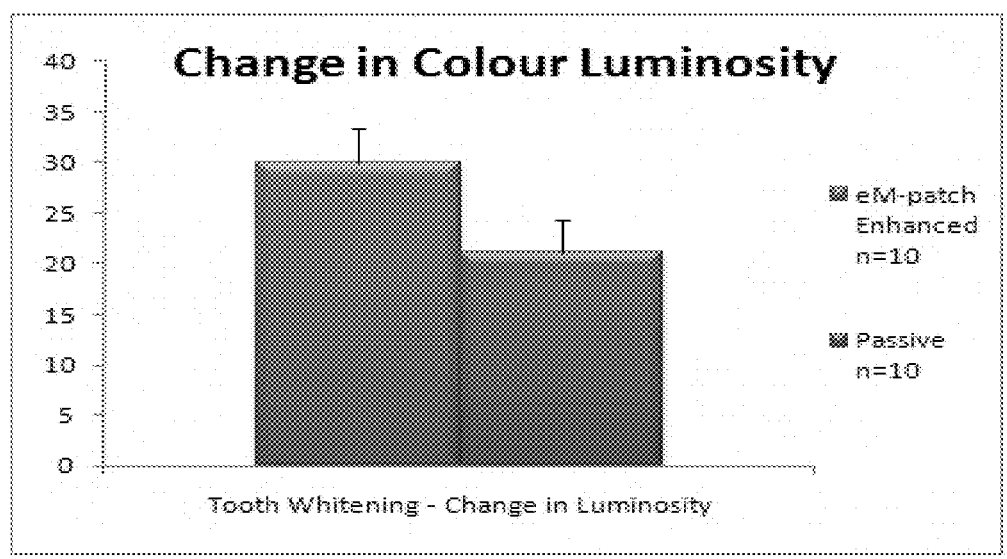
FIG. 9 is a graph of the change in colour luminosity of teeth treated with carbamide peroxide delivered passively or by a device of the present invention.

Luminosity analysis also showed a statistically significant difference between the groups, with the group exposed to the exposed to the pairs of displaced dipolar magnetic elements in motion achieving 40% greater increase in luminosity than the passive group (Table 3 and FIG. 9).

TABLE 3

|  | Magnetic FIM (eM-pach) | Passive |
|---|---|---|
| Mean | 29.54 | 21.09 |
| Stdev | 9.55 | 9.17 |
| Sem | 3.38 | 3.24 |

$p = 0.023$

Example 2

Figure 11:
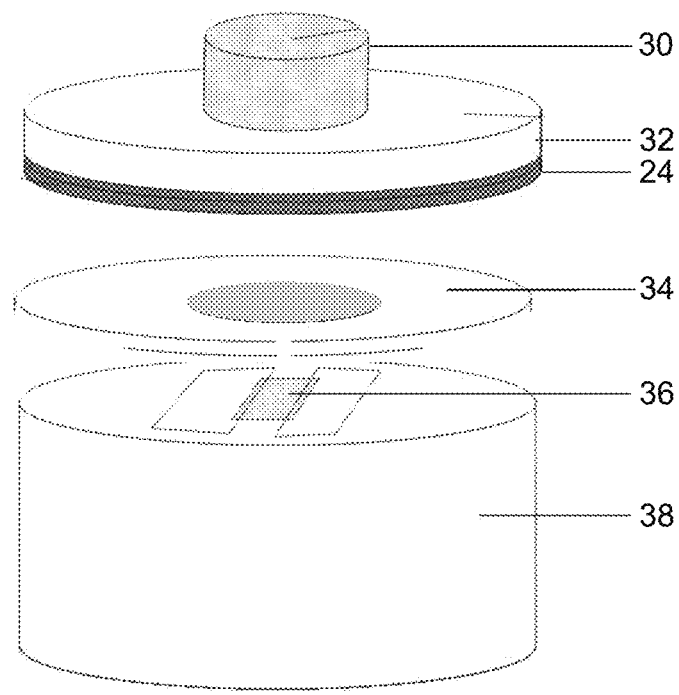
FIG. 11 shows position of the displaced dipolar magnetic elements over the enamel block. In operation the gap between the magnet and the lesion is approx 1.8 mm. Features shown include a handle 30, a Perspex disc 32, a sheet of pairs of displaced dipolar magnetic elements 24, a nylon washer 34 with 250 ppm F methyl cellulose gel, an exposed enamel lesion 36, and a block 38.

This study was designed to examine the ability of parallel and oriented arrays of displaced dipolar magnetic element to drive fluoride ions from within a methyl cellulose gel into a lesion 36 in the enamel of a tooth surface (see FIG. 11). The experiment explored two types of displaced dipolar magnetic elements: oriented pairs of displaced dipolar magnetic elements; and a linear pairs of the same displaced dipolar magnetic elements. Discs comprising the same base material but with no magnetic field or displaced dipolar magnetic elements were used as a negative control.

Materials and Instruments

Displaced Dipolar Magnetic Elements

ETP008—a linear array of displaced dipolar magnetic elements comprising strontium oxides dispersed in a poly-propylene-film base. The displaced dipolar magnetic elements were created in parallel with a pole flux of 450 gauss. Each element or pole was 2.7 mm wide, creating a pair of displaced dipolar magnetic elements of pitch of 1.5 pairs per centimeter. Inter-pair flux gradient was 900 gauss or 1350 gauss per centimeter.

ETP012—an oriented array of displaced dipolar magnetic elements comprising strontium oxides dispersed in a poly-propylene film base. The oriented displaced dipolar magnetic elements were created by drawing a secondary flux pattern over the linear pattern comprising 2.0 mm poles, creating a pair of displaced dipolar magnetic elements of pitch of 2.5 pairs per centimeter. Inter-pair flux gradient was 700 gauss or 1750 gauss per centimeter. The secondary field elements oriented at 90 degrees top the primary, consisted of parallel pairs of displaced dipolar magnetic elements of pitch of 1.5 mm, creating 3.5 pairs per centimeter, with 300 gauss per centimeter oriented flux. The resulting oriented displaced dipolar magnetic elements create a differentially oriented magnetic flux pattern.

Acid Gel Preparation

Demineralised of tooth enamel to form lesions was performed using the standard GSK methyl cellulose/lactic acid system. An 8% methyl cellulose (aqueous, 1500 cPs, 63 kDa, Fisher Chemicals, UK) solution was made up and poured over the enamel specimens (teeth) to a height of 25 mm above the specimens. When set, a 0.1M, pH 4.6 solution of lactic acid was poured on top to a depth of 25 mm.

The acid gel system was then placed into an incubator at 37° C. for 19 days.

Methyl Cellulose Gel Preparation

Figure 12:
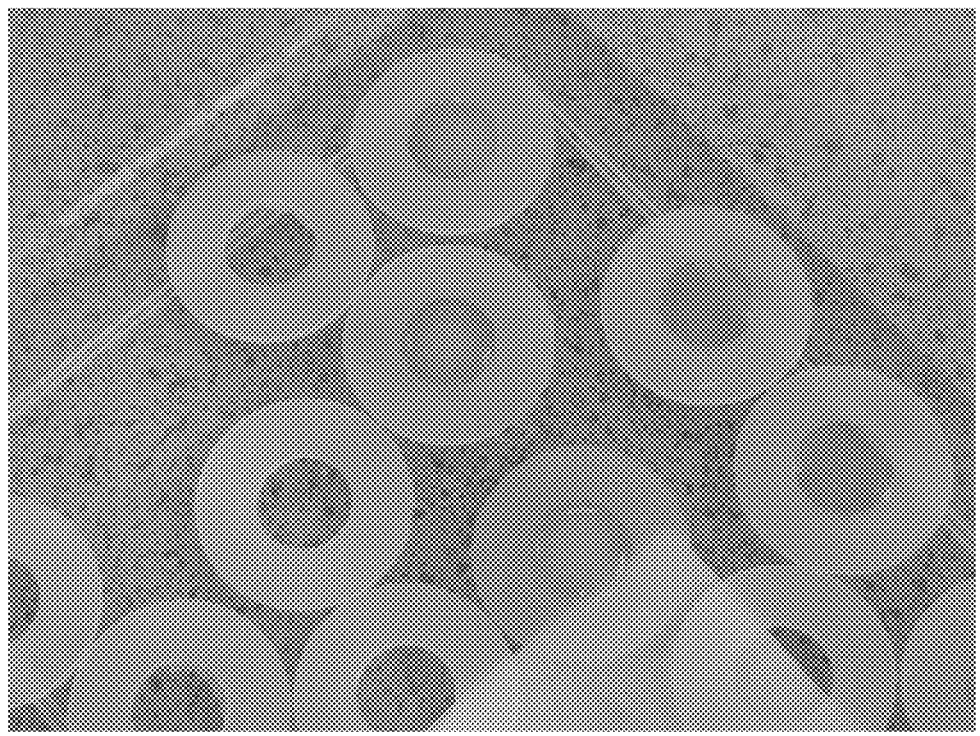
FIG. 12 shows the methyl cellulose gel within the nylon washer. The photograph shows washers with and without gel.
Figure 13A:
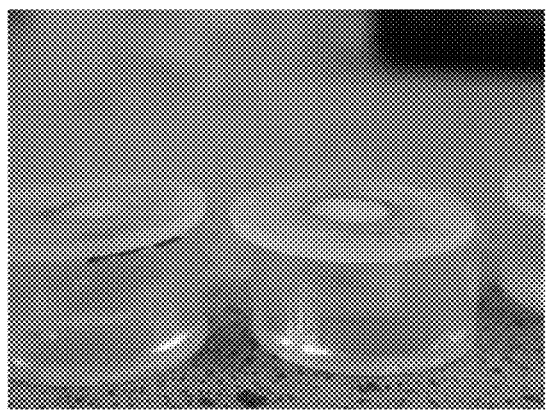
FIGS. 13A and 13B show the methyl cellulose gel placed over the bovine enamel lesion.
Figure 13B:
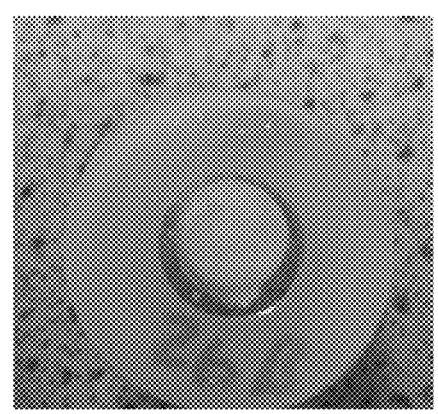

Methyl cellulose gel was prepared with NaF to give a fluoride concentration in the final slurry of 250 ppm F. The methyl cellulose fluoride slurry was cast into nylon washers (1.6 mm thick, 12 mm diameter central hole) to give a uniform thickness, and left at 5° C. overnight to set (see FIG. 12). When ready for use, the methyl cellulose disks were placed directly onto the surface of the enamel lesion in the bovine tooth (see FIG. 13).

Analysis Techniques

Fluoride analysis was performed using the ThermoOrion ion plus combination fluoride electrode 9609BN ion selective electrode (ISE) together with an ELIT 9804 electrode meter.

Solution pH was determined using a Metier Toledo pH electrode inlab413 with a Hanna pH meter.

Masses were determined using an Acculab Satorius balance.

Reagents

Deionised (DI) water was supplied on tap and is RO purified and deionised.

Sodium fluoride was from BDH (lot number 923446 439, exp July 2015); Methyl cellulose was from Sigma (lot number 029k0192); Potassium hydroxide was from Sigma (lot number 028k07551 exp June 2012); Perchloric acid was from Aldrich (lot 29196DK, exp June 2012); Lactic acid was from Sigma (lot 128K1349, exp December 2013); Sodium acetate supplied by GSK (lot 71550, exp March 2013).

Bovine incisors were sourced from F. Conisbee, Leatherhead, Surrey and are certified BSE free.

Method

Enamel lesions in bovine teeth were prepared as described above.

Time Course Groups

An initial time course study was performed where the fluorinated methyl cellulose disks were placed onto lesions (n=8), for 30, 60 and 120 minutes to determine an optimal incubation time for there to be an appreciable fluoride uptake into the lesion. At the end of the time period, the gel was removed from the enamel specimens by rinsing under DI water, and then the enamel specimens were placed into DI water for 17 hours. They were then dried, ready for the fluoride extraction step.

Study Groups

The investigation was made up of three study groups:
1) Static linear displaced dipolar magnetic element array ETP008;
2) Static oriented displaced dipolar magnetic element array ETP012;
3) Static negative control (with Perspex disk);

Two types of displaced dipolar magnetic elements were used: oriented and linear arrays. For each of these arrays, seven specimens were set up by placing the arrays on top of the fluoride methyl cellulose gel that was in turn placed on top of the enamel lesion. The gel/magnetic arrays were then left for 120 minutes on the enamel specimen. The gel was then rinsed off the enamel specimens under DI water and then the enamel specimens were left to soak in DI water overnight (17 hours), followed by drying in preparation for the fluoride extraction step.

In the Negative control group, the fluorinated methyl cellulose gel was sandwiched between the lesion and a blank Perspex disc (replacing the magnetic array) for 120 minutes. The gel was then rinsed off and the specimens left to soak etc as in the previous group.

Fluoride Extraction

The enamel specimens were painted with nail varnish outside of the lesion to form a well. Fluoride was extracted from the lesion following the procedure outlined in Lynch and Duckworth (Caries Res. 1998, 32, 417-421). 100 ul of a 1 molar solution of perchloric acid was applied to the lesion for 15 minutes. After 15 minutes, the acid was aspirated off and the lesion rinsed with three 100 ul applications of a 1 molar solution of sodium acetate. The washing then added to the aspirated acid together with a further 200 ul of perchloric acid. The solutions were stored in pre weighed 7 ml Bijou universal container and re-weighed after the fluoride extraction steps. They were then stored until the fluoride analysis step, see below.

Fluoride Analysis

Fluoride ion analysis was performed using a single junction combination ion selective electrode (ISE). The method follows that of Shen-xun Shi et al (Anal. Sci., 2003, 1.9, 5, 671) where the electrode is first activated by placing it into a 0.5M solution of perchloric acid, overnight. Subsequent measurements of fluoride are performed in solutions that contain perchloric acid and sodium acetate, the latter acts as a total ion adjustment buffer and maintain a constant pH, in this case, pH4.0. Shen-xun Shi et al have reported that there is a linear Nernst behaviour down to $1 \times 10^{-7}$ mols dm$^{-3}$ using the method described.

In this study, a calibration was performed using a serial dilution of the same ratio of sodium acetate and perchloric acid as that used in the study. A n=4 calibration curve for fluoride solutions ranging from $7.3 \times 10^{-7}$ to $7.3 \times 10^{-3}$ mols dm$^{-3}$ gave a linear fit ($r^2$) of 0.9872.

The solution from the enamel lesion studies above were measured by inserting the ISE directly into the Bijou and observing the mV reading until linear (approx. 1-2 minutes). When linear, the mV reading was recorded in an EXCEL spreadsheet (Excel File ML35, Modus Laboratories) and the concentration determined from the calibration curve.

Results

Figure 14:
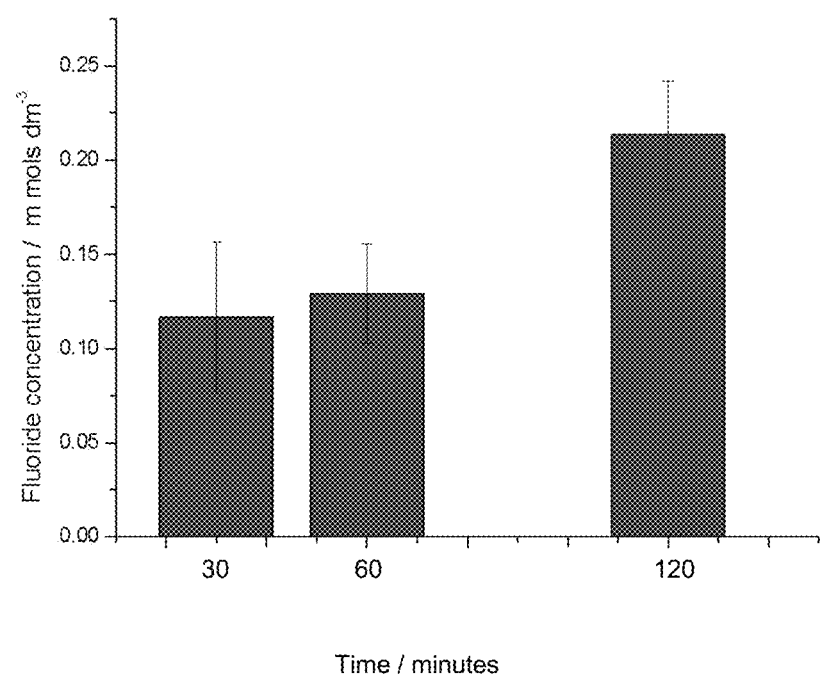
FIG. 14 is a graph showing the fluoride uptake into bovine enamel lesions from MC gel comprising 250 ppm F; samples taken at 30, 60 and 120 minutes. n=8.

The fluoride concentrations resulting from the extracted lesions for the time course study are shown in Table 4 and in graphical format in FIG. 14. From these results it was decided that the incubation time for the experimental study should be 120 minutes. This is considerably longer than the incubation time for the aqueous fluoride study in ML28 and is a reflection of the reduction in fluoride mobility when made up in a methyl cellulose gel system.

TABLE 4

| Incubation time/min | Mean value m mol dm−3 | Mean Diff | Sig | Prob |
|---|---|---|---|---|
| 30 | 1.18E−4 | 1.2E−5 | 0.73 | 0 |
| 60 | 1.31E−4 | 9.5E−5 | 3.26E−5 | 1 |
| 120 | 2.14E−4 | 8.3E−5 | 2.73E−4 | 1 |

At the 0.05 level the 30 and 60 minute groups are significantly different from the 120 minute group.

Figure 15:
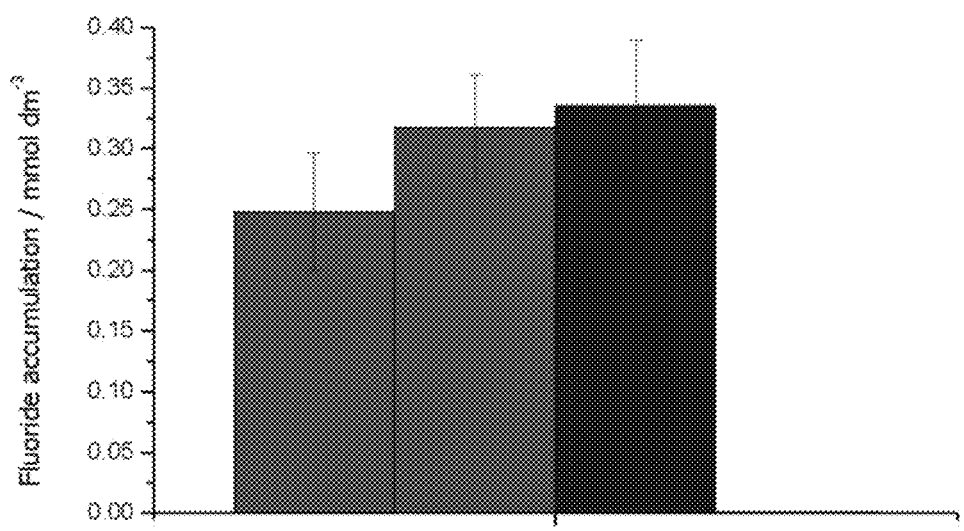
FIG. 15 is a graph of the mean values for the extracted fluoride concentrations for each of the experimental groups, indicating the fluoride uptake of the lesions under the influence of magnetic arrays of, the invention.

Each solution in the time course and the experimental study was measured three times and the results recorded in and EXCEL spreadsheet. Details can be found in the LNB Modus Laboratories 00001 page 71. The average mV readings were calculated and converted into concentration values via the calibration constant and the dilution factor. The results of the fluoride uptake for the experimental study are shown in Table 5 and FIG. 15.

TABLE 5

| Sample group | Sample size | Mean fluoride uptake mols dm-3. | SD |
|---|---|---|---|
| Negative control | 7 | 2.49E−4 | 4.75E−5 |
| ETP012 Static oriented array | 7 | 3.17E−4 | 4.34E−5 |
| ETP008 Static linear array | 7 | 3.35E−4 | 5.35E−5 |

Statistical Evaluation

A statistical evaluation of the data sets was performed using one way ANOVA and Tukey means comparison. Data sets were first tested for normal distribution using Shapiro-Wilks normality test. All data sets had a probability factor greater than 0.05 indicating they were normally distributed. In addition to the one way ANOVA, Dr. Lynch performed an additional statistical evaluation, multiple range test, on the results, a summary of which is below.

TABLE 6

Pair wise means comparison for the experimental study group.

| | Mean Diff | q Value | Prob | Sig | LCL | UCL |
|---|---|---|---|---|---|---|
| ETP012 Static Oriented v Negative control | 6.97E−05 | 3.54 | 0.09 | 0 | −7.17E−06 | 1.47E−04 |
| ETP008 Static Linear v Negative control | 8.76E−05 | 4.44 | 0.02 | 1 | 1.07E−05 | 1.64E−04 |
| ETP008 Static Linear v ETP012 Static Oriented | 1.79E−05 | 0.91 | 0.92 | 0 | −5.90E−05 | 9.48E−05 |

Sig = 1 indicates that the means difference is significant at the 0.05 level
Sig = 0 indicates that the means difference is not significant at the 0.05 level Fluoride uptake into bovine enamel lesions from a 250 ppm fluorinated methyl cellulose gel was found to be 0.25 mmol dm$^{-3}$. On repeating the experimental procedure with the addition of a magnetic disc the concentration of fluoride uptake increased to 0.31 and 0.33 mmol dm$^{-3}$ for the oriented and linear displaced dipolar magnetic element, respectively.

A statistical analysis was used to test the significance of the differences between the treatment groups. A one way ANOVA and Tukey means comparison shows that the treatment groups with either the linear (P=0.02) or the oriented (p=0.08) magnetic array give a higher fluoride uptake compared to the group without the magnet. Note that the oriented array is just outside the 0.05 level but further statistical models using Kruskal-Wallis analysis confirmed a statistical difference.

Numerous variations and modifications will suggest themselves to persons skilled in the relevant technical arts, in addition to those already described, without departing from the basic inventive concepts. All such variations and modifications are to be considered within the scope of the present invention, the nature of which is to be determined from the foregoing description.

The claims defining the invention are as follows:

1. A method for the delivery by diamagnetic repulsion enhanced diffusion of an oral care active agent comprising:
    applying an active agent(s) between a target oral biological barrier and a magnetic device, the magnetic device comprising at least a first set of pairs of displaced dipolar magnetic elements and a second set of pairs of displaced dipolar magnetic elements,
    wherein the pairs of displaced dipolar magnetic elements have surfaces linked by a magnetic return,
    wherein the magnetic return is orientated on the surfaces of the pairs of displaced dipolar magnetic elements distal to the biological barrier,
    wherein a magnetic flux of each magnetic pole of the pairs of displaced dipolar magnetic elements is between 100 Gauss and 600 Gauss and wherein the poles in a spatial region are between 1.0 mm and 5.0 mm apart, and
    wherein the first set of pairs of displaced dipolar magnetic elements forms a layer and the second set of pairs of displaced dipolar magnetic elements forms a separate spatial layer relative to the first set of pairs of displaced dipolar magnetic elements, said spatial layers being arranged in parallel to the oral biological barrier,
    wherein the spatial layers are arranged such that the first spatial layer is stacked on the target oral biological barrier and the second spatial layer is stacked on top of the first layer more distal to the barrier than the first layer,
    wherein alignment of the first spatial layer comprising the first set of pairs of displaced dipolar magnetic elements is angularly offset between 1° and 90° relative to the second spatial layer comprising the second set of pairs of displaced dipolar magnetic elements, and
    wherein the angular offset of the first spatial layer comprising the first set of pairs of displaced dipolar magnetic elements to the second spatial layer comprising the second set of pairs of displaced dipolar magnetic elements results in multiple intersections of magnetic fields and multiple regions of magnetic flux gradient, and
    moving in a reciprocal or rotational manner the magnetic device so that active agents in proximity to said device will be subject to alternating polarities of magnetic field and alternating magnetic flux gradients in response to said reciprocal or rotational movement.

2. The method according to claim 1 wherein the magnetic device includes an electronic or mechanical means for moving the magnetic device over the biological barrier.

3. The method according to claim 1 wherein the movement of the magnetic device has an oscillation frequency of 1 Hz to 5 Hz and the strength of the magnet field produced by each magnetic element is between 100 and 500 Gauss.

4. The method according to claim 1 wherein the movement of the magnetic device has an oscillation frequency of 100 to 8,000 Hz and the strength of the magnet field produced by each magnetic element is between 100 and 600 Gauss.

5. The method according to claim 1 wherein each pair of displaced dipolar magnetic elements is disposed at a repetition rate of between 2 and 10 dipolar pairs per centimeter.

6. The method according to claim 1 wherein each pair of displaced dipolar magnetic elements is disposed at a repetition rate of between 1.5 and 4 dipolar pairs per centimeter.

7. The method according to claim 1 wherein the magnetic flux of each magnetic pole is between 125 to 450 Gauss.

8. The method according to claim 1 wherein a delta magnetic flux between two adjacent poles of opposite polarity is between 100 Gauss and 2000 Gauss.

9. The method according to claim 8 wherein the delta magnetic flux between two adjacent poles of opposite polarity is 200 to 900 Gauss.

10. The method of claim 1 wherein the angular offset of the first spatial layer comprising the first set of pairs of displaced dipolar magnetic elements is at least 45° relative to the second spatial layer comprising the second set of pairs of displaced dipolar magnetic elements.

11. The method of claim 1 wherein the device is in the form of one of the following: a brush, a pad, a mouthguard, a dental splint, a roller applicator or a pen device.

12. The method of claim 1 wherein the active agent is applied to the oral biological barrier prior to application of the magnetic device.

13. The method of claim 1 wherein the active agent is applied to the magnetic device prior to application of the magnetic device to the oral biological barrier.

* * * * *

UNITED STATES PATENT AND TRADEMARK OFFICE
CERTIFICATE OF CORRECTION

| | | |
|---|---|---|
| PATENT NO. | : 9,452,037 B2 | Page 1 of 1 |
| APPLICATION NO. | : 13/699225 | |
| DATED | : September 27, 2016 | |
| INVENTOR(S) | : Jeffrey D. Edwards | |

It is certified that error appears in the above-identified patent and that said Letters Patent is hereby corrected as shown below:

In the Specification

At Column 10, Line 7, "magnet field" should be -- magnetic field --.

In the Claims

At Column 22, Line 16, "apart, and" should be -- apart, --.

At Column 22, Line 50, "magnet field" should be -- magnetic field --.

At Column 22, Line 54, "magnet field" should be -- magnetic field --.

Signed and Sealed this
Eleventh Day of April, 2017

Michelle K. Lee
*Director of the United States Patent and Trademark Office*